(12) United States Patent
Findley et al.

(10) Patent No.: US 9,090,404 B2
(45) Date of Patent: Jul. 28, 2015

(54) CARRIER MEMBER HAVING A RESILIENT MEMBER

(71) Applicant: The Procter & Gamble Company, Cincinnati, OH (US)

(72) Inventors: Daniel Patrick Findley, Finneytown, OH (US); Uwe Schneider, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 104 days.

(21) Appl. No.: 13/949,326

(22) Filed: Jul. 24, 2013

(65) Prior Publication Data
US 2015/0027853 A1    Jan. 29, 2015

(51) Int. Cl.
B65G 15/14       (2006.01)
B65G 37/00       (2006.01)
A61F 13/15       (2006.01)

(52) U.S. Cl.
CPC .......... *B65G 37/00* (2013.01); *A61F 13/15577* (2013.01)

(58) Field of Classification Search
USPC ....................................................... 198/605
See application file for complete search history.

(56) References Cited

U.S. PATENT DOCUMENTS

| | | | | |
|---|---|---|---|---|
| 1,749,393 A | * | 3/1930 | Pflimlin | 492/57 |
| 3,449,548 A | * | 6/1969 | Adamek et al. | 219/216 |
| 4,425,694 A | * | 1/1984 | Somerville | 271/272 |
| 4,523,674 A | * | 6/1985 | Haugen et al. | 198/843 |
| 4,629,457 A | | 12/1986 | Ness et al. | |
| 4,823,689 A | * | 4/1989 | Kishino et al. | 100/155 R |
| 5,251,742 A | * | 10/1993 | Campbell | 198/841 |
| 7,569,039 B2 | | 8/2009 | Matsuda et al. | |
| 7,587,966 B2 | | 9/2009 | Nakakado et al. | |
| 8,607,959 B2 | | 12/2013 | Papsdorf et al. | |
| 8,720,666 B2 | | 5/2014 | Papsdorf et al. | |
| 8,820,513 B2 | | 9/2014 | Papsdorf et al. | |
| 8,833,542 B2 | | 9/2014 | Papsdorf et al. | |
| 2005/0107764 A1 | | 5/2005 | Matsuda et al. | |
| 2007/0219521 A1 | | 9/2007 | Hird et al. | |
| 2010/0151191 A1 | | 6/2010 | Thomas et al. | |
| 2011/0139657 A1 | | 6/2011 | Hird et al. | |
| 2011/0139658 A1 | | 6/2011 | Hird et al. | |
| 2011/0139659 A1 | | 6/2011 | Hird et al. | |
| 2011/0139662 A1 | | 6/2011 | Hird et al. | |
| 2011/0152812 A1 | | 6/2011 | Hird et al. | |

(Continued)

OTHER PUBLICATIONS

PCT International Search Report dated Sep. 22, 2014, 9 pages.

(Continued)

*Primary Examiner* — William R Harp
(74) *Attorney, Agent, or Firm* — Sarah M. DeCristofaro; Abbey A. Lopez

(57) ABSTRACT

A carrier member is configured to receive a discrete article from a transfer assembly. The carrier member includes a cylindrical roll having a receiving surface and a resilient member connected with the receiving surface. The resilient member has a plurality of intermittently spaced first voids extending circumferentially about the axis of rotation at a first radial distance from the axis of rotation and a plurality of intermittently spaced second voids extending circumferentially about the axis of rotation at a second radial distance from the axis of rotation. The first radial distance is greater than the second radial distance. Each first void is separated from each second void.

17 Claims, 12 Drawing Sheets

(56) References Cited

U.S. PATENT DOCUMENTS

2012/0061015 A1 3/2012 LaVon et al.
2012/0061016 A1 3/2012 LaVon et al.

OTHER PUBLICATIONS

U.S. Appl. No. 61/717,302, filed Oct. 23, 2012, Uwe Schneider, et al.

* cited by examiner

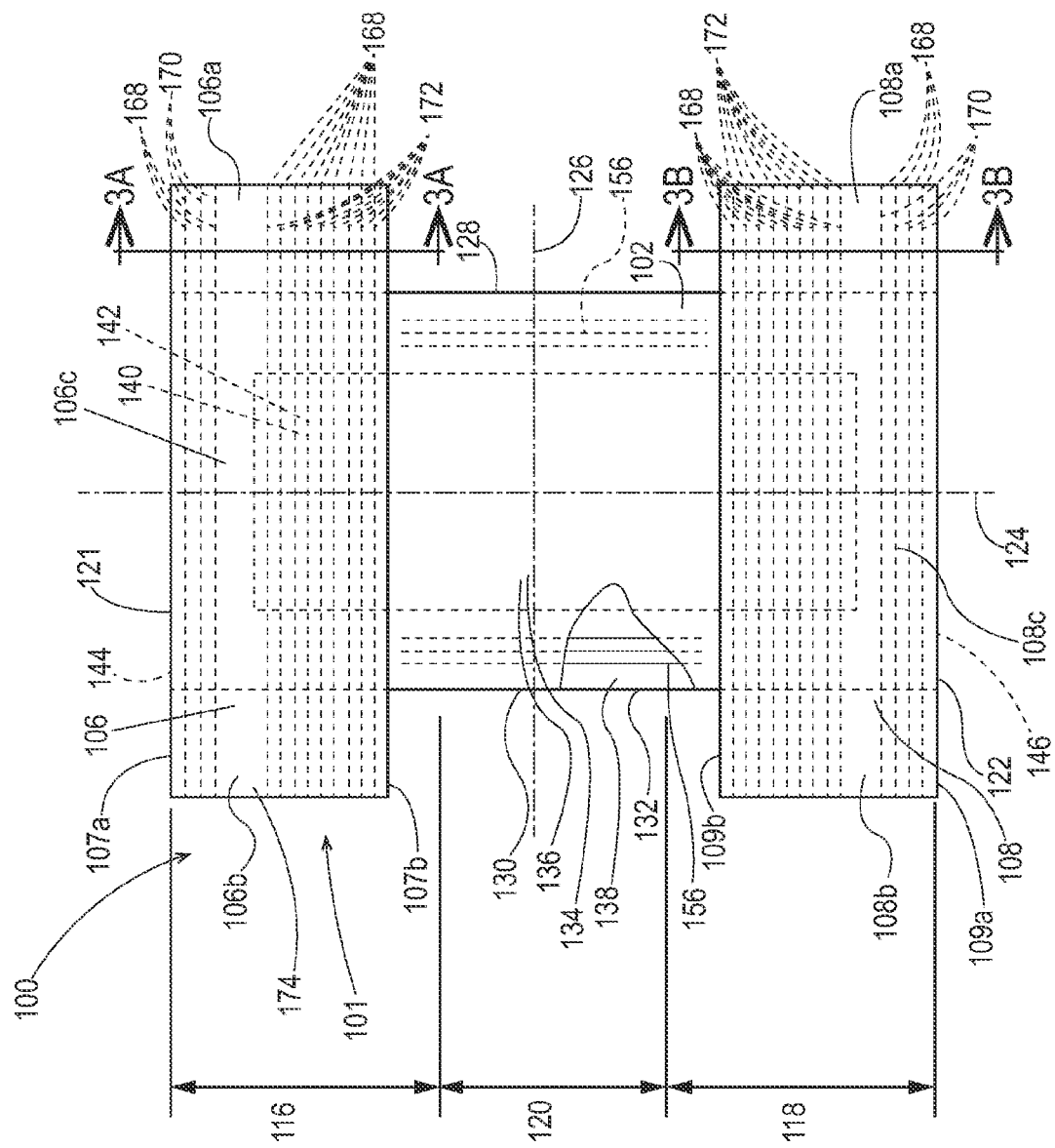

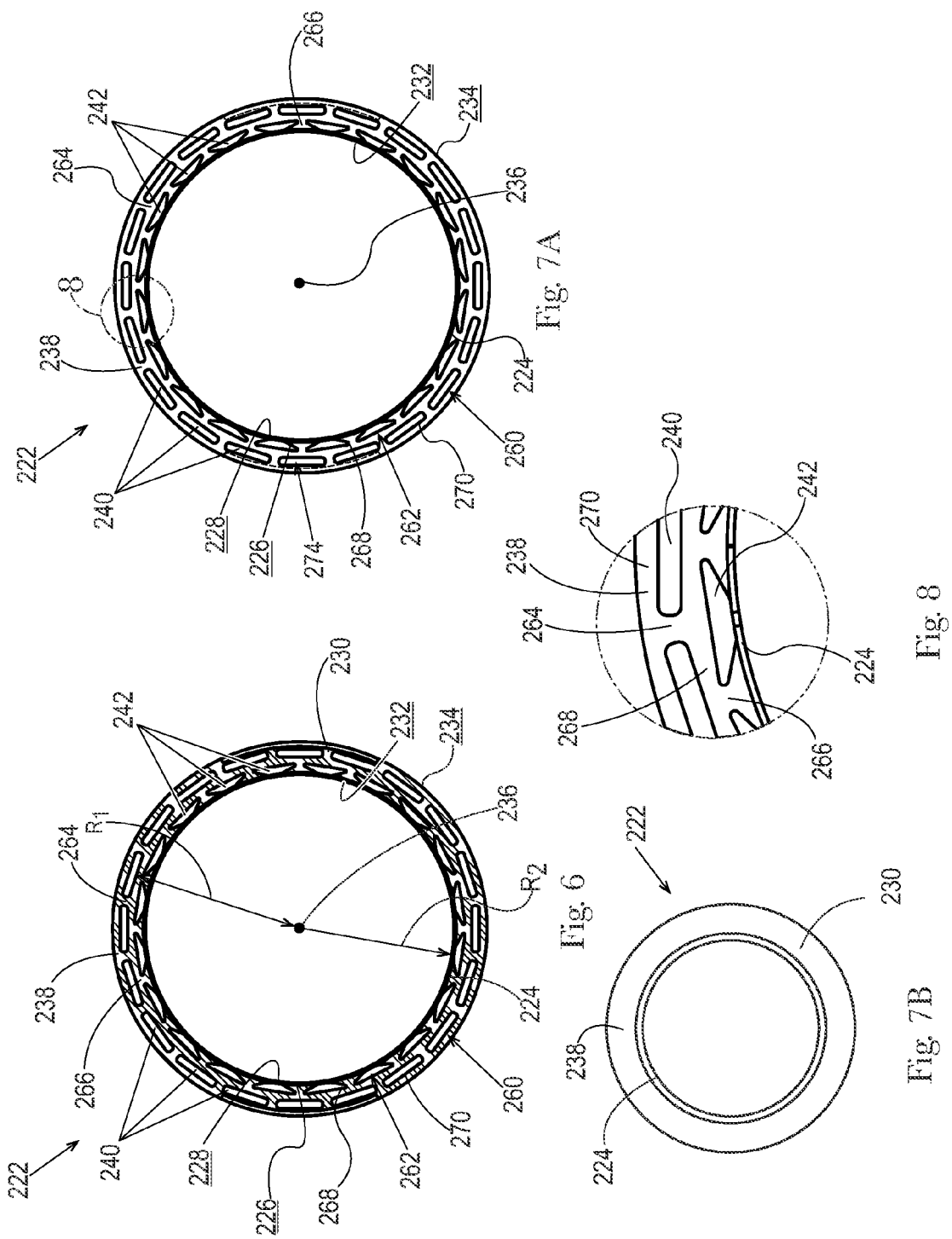

CARRIER MEMBER HAVING A RESILIENT MEMBER

FIELD

The present disclosure generally relates to an apparatus for manufacturing absorbent articles, and, more particularly, relates to a carrier member having a resilient member for joining components of absorbent articles.

BACKGROUND

Absorbent articles, such as taped diapers or pant diapers, for example, may be manufactured by a process where discrete articles, such as a chassis of a taped diaper or a pant diaper including a topsheet, a backsheet, and an absorbent core, for example, are applied to one or more moving webs of components, such as webs of front and rear belt portions, for example, using transfer members of a transfer assembly. Often, a speed at which the discrete articles are fed onto the transfer assembly is not the same as a speed of a carrier member on which the moving webs of components are situated. Thus, the speed of the discrete articles should generally be changed by the transfer assembly to match, or closely match, the speed of the one or webs of components being conveyed over the carrier member to properly join the discrete articles to the one or more webs of components without adversely affecting the process or a finished product produced by the process. In some instances, the discrete articles may also need to be turned (e.g., about 90 degrees) and repitched by the transfer assembly after pickup from the cutting device and before placement onto the webs conveyed over the carrier member. A transfer assembly may rotate about an axis of rotation and may include a plurality of transfer members rotatable about an axis of rotation.

In some processes, a nip is formed between the carrier member and each transfer member in order to apply a force to the discrete article sufficient to join each discrete article advancing on a transfer member with the moving web. However, the surface of the transfer member may have a different shape than the surface of the carrier member. As a result, the force applied at the nip may vary over time, and portions of the transfer member may cause intermittent spikes in force at the nip. Consequently, the increase in force may cause accelerated wear to the transfer assembly that requires relatively frequent changeover of worn parts. Additionally, the changes in force may result in a non-uniform bond between the discrete component and the moving web.

Thus, it would be beneficial to provide an apparatus for transferring discrete articles to a moving web by applying a relatively low and substantially uniform force at a nip between a transfer assembly and a carrier member.

SUMMARY

Aspects of the present disclosure may include a carrier member configured to receive a discrete article from a transfer assembly. The carrier member may comprise a body having an outer surface and a resilient member connected with the outer surface of the body. The resilient member comprises a resilient material; a first row of intermittently spaced first voids; and a second row of intermittently spaced second voids. Each first void in the first row is offset from adjacent second voids in the second row. Each first void is separated from each second void by the resilient material.

Aspects of the present disclosure may include an apparatus comprising a transfer member having an outer surface; and a carrier member comprises a body having an outer surface and a resilient member connected with the outer surface of the body. The carrier member may be rotatable about an axis of rotation. The resilient member may comprise a resilient material, a plurality of intermittently spaced first voids extending circumferentially about the axis of rotation at a first radial distance from the axis of rotation, and a plurality of intermittently spaced second voids extending circumferentially about the axis of rotation at a second radial distance from the axis of rotation. The first radial distance may be greater than the second radial distance. A nip is formed between the cylindrical roll and the transfer member.

Aspects of the present disclosure may include a carrier member configured to receive a discrete article from a transfer assembly. The carrier member may comprise a body having an outer surface and a resilient member connected with the outer surface of the body. The carrier member may be rotatable about an axis of rotation. The resilient member may comprise a plurality of intermittently spaced first voids extending circumferentially about the axis of rotation at a first radial distance from the axis of rotation. The resilient member may comprise a plurality of intermittently spaced second voids extending circumferentially about the axis of rotation at a second radial distance from the axis of rotation. The first radial distance may be greater than the second radial distance. The first voids are separated from the second voids.

BRIEF DESCRIPTION OF THE DRAWINGS

FIG. 2B is a partially cut-away, plan view of a diaper pant.
FIG. 6 is a cross-sectional view of the carrier member of FIG. 5 taken along line 6-6.
FIG. 7A is a front, elevation view of a carrier member having a body and a resilient member connected with the body.
FIG. 7B is a front, elevation view of a carrier member having a body and a resilient member connected with the body.
FIG. 8 is a magnified view of the carrier member of FIG. 7A.

DETAILED DESCRIPTION

Figure 1:
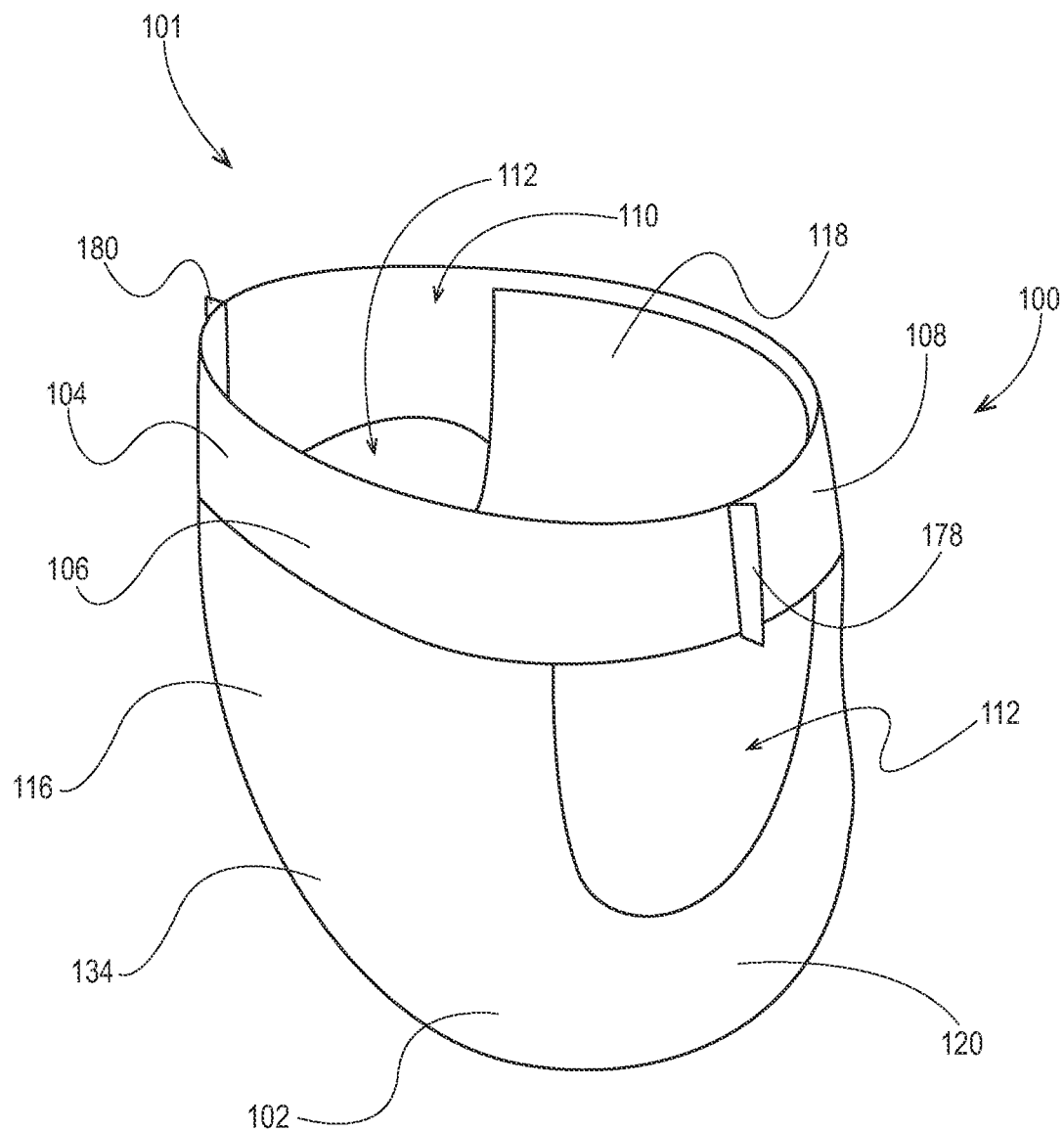
FIG. 1 is a schematic, perspective view of a diaper pant.

Various non-limiting exemplary configurations of the present disclosure will now be described to provide an overall understanding of the principles of the structure, function, manufacture, and use of the apparatuses for transferring discrete articles disclosed herein. One or more examples of these non-limiting exemplary configurations are illustrated in the accompanying drawings. Those of ordinary skill in the art will understand that the apparatuses for transferring discrete articles described herein and illustrated in the accompanying drawings are non-limiting example configurations and that the scope of the various non-limiting configurations of the present disclosure are defined solely by the claims. The features illustrated or described in connection with one non-limiting exemplary configuration may be combined with the features of other non-limiting exemplary configurations. Such modifications and variations are intended to be included within the scope of the present disclosure.

"Absorbent article" is used herein to refer to consumer products that primarily functions to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (for example, they are intended to be discarded after a single use and may also be configured to be recycled, composted or otherwise disposed of in an environmentally compatible manner).

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

"Substrate" is used herein to describe a material which is primarily two-dimensional (i.e. in an XY plane) and whose thickness (in a Z direction) is relatively small (i.e. 1/10 or less) in comparison to the substrate's length (in an X direction) and width (in a Y direction). Non-limiting examples of substrates include a web, layer or layers or fibrous materials, nonwovens, films and foils such as polymeric films or metallic foils. These materials may be used alone or may comprise two or more layers joined together. As such, a web is a substrate.

"Nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

"Machine direction" (MD) is used herein to refer to the direction of material flow through a process. In addition, relative placement and movement of material can be described as flowing in the machine direction through a process from upstream in the process to downstream in the process. "Cross direction" (CD) is used herein to refer to a direction that is not parallel with, and usually perpendicular to, the machine direction.

"Pant" (also referred to commercially as "training pant", "pre-closed diaper", "pant diaper", "diaper pant", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (for example, seams, heat bonds, pressure welds, adhesives, cohesive bonds, mechanical fasteners, etc.). A pant can be preformed anywhere along the circumference of the article in the waist region (for example, side fastened or seamed, front waist fastened or seamed, rear waist fastened or seamed).

The present disclosure includes an apparatus for joining discrete components, such as a chassis of an absorbent article, advancing in a machine direction to a continuous web or webs, such as a continuous waistband or waistbands, advancing in the machine direction. The apparatus may include a transfer assembly including at least one transfer member having an outer surface. The transfer member may advance the discrete components from a cutting device where the discrete components may be cut from a continuous substrate to a carrier member where the discrete components may be joined with the continuous web or webs advancing in the machine direction. The transfer assembly may turn and/or repitch the discrete component from a first orientation to a second orientation intermediate the cutting device and the carrier member. In addition, the transfer assembly may speed up the discrete component from advancing at a first speed on the cutting device to a second, faster speed at the carrier member. Then, the transfer assembly may advance the discrete component to the carrier member where the discrete component is joined with the advancing continuous web or webs.

The carrier member may comprise a body having an outer surface and a resilient member connected with the outer surface of the body. The resilient member comprises a resilient material, a first row of intermittently spaced first voids, and a second row of intermittently spaced second voids. Each first void in the first row may be offset from adjacent second voids in the second row. Each first void may be separated from each second void by the resilient material. The carrier member may be positioned adjacent to the transfer assembly so as to create an installed interference between the carrier member and the transfer member at a nip.

In operation, the transfer assembly advances the discrete component to the nip between the transfer member and the carrier member. As a result of advancing the discrete component through the nip, the installed interference between the transfer member and the carrier member causes the resilient member to compress by a degree sufficient to bond the discrete component to the advancing continuous webs. As a result of the resilient member compressing under the applied force, the force applied to the transfer member is minimized, and the life of the transfer assembly may be extended. In addition, staggering the first row of first voids and the second row of second voids may allow for a relatively uniform force being applied to the discrete component and to the transfer member, and, thus, a relatively uniform bond between the discrete component and the advancing web or webs.

In some exemplary configurations, the carrier member may be configured in the form of a cylindrical roll. In such an exemplary configuration, the resilient member may comprise a plurality of intermittently spaced first voids extending circumferentially about the axis of rotation at a first radial distance from the axis of rotation and a plurality of intermittently spaced second voids extending circumferentially about the axis of rotation at a second radial distance from the axis of rotation. The first radial distance may be greater than the second radial distance. Each first void may be separated from each adjacent second void.

It is to be appreciated that the methods and apparatuses of the present disclosure may also be suitable for any other uses that require joining a discrete component with an advancing substrate or substrate regardless of whether the discrete articles or discrete components need to be turned and/or repitched, and regardless of the speed of the carrier member. These other uses may comprise various manufacturing processes for any product, or intermediate product, in any industry.

As discussed above, the apparatuses disclosed herein may be used to join discrete articles with advancing continuous webs, some of which may be used in the manufacture of different types of absorbent articles. To help provide additional context to the subsequent discussion, the following provides a general description of absorbent articles in the form of diapers that include components that may be joined in accordance with the apparatuses and methods disclosed herein.

Figure 2A:
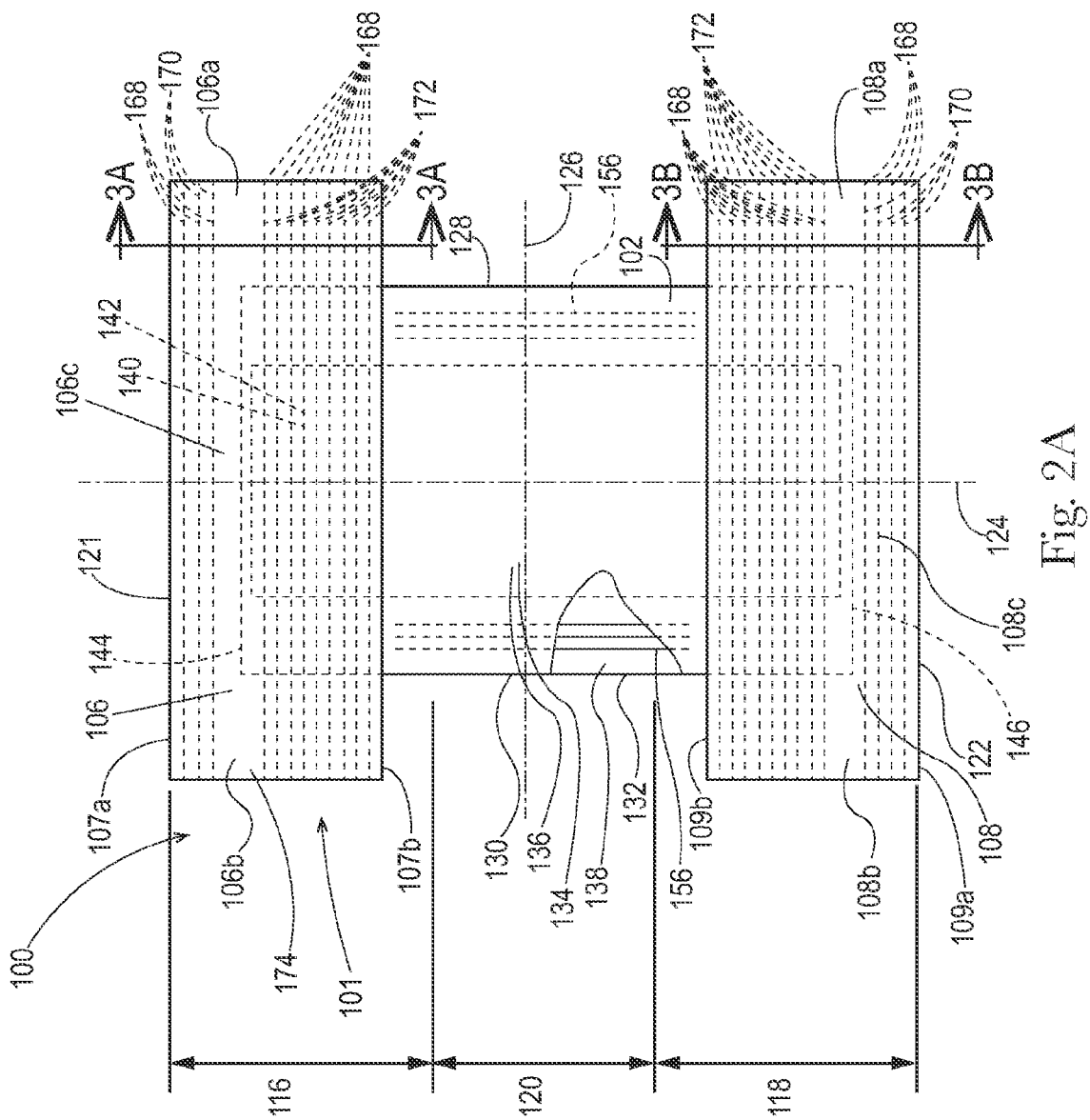
FIG. 2A is a partially cut-away, plan view of a diaper pant.

FIGS. 1, 2A, and 2B show an exemplary absorbent article 100 in the form of a diaper pant 101 that may be formed in accordance with the apparatuses and methods disclosed herein. In particular, FIG. 1 shows a perspective view of a diaper pant 101 in a pre-fastened configuration and FIGS. 2A and 2B show plan views of the diaper pant 101 with the portion of the diaper pant 101 that faces away from a wearer oriented toward the viewer. The diaper pant 101 shown in FIG. 1 includes a chassis 102 and a ring-like elastic belt 104. As discussed below in more detail, a first elastic belt 106 and a second elastic belt 108 are connected together to form the ring-like elastic belt 104.

With continued reference to FIG. 2A, the chassis 102 includes a first waist region 116, a second waist region 118, and a crotch region 120 disposed intermediate the first and second waist regions 116 and 118. The first waist region 116 may be configured as a front waist region, and the second waist region 118 may be configured as back waist region. In some embodiments, the length of each of the front waist region 116, back waist region 118, and crotch region 120 may be one-third of the length of the absorbent article 100. The diaper pant 101 may also include a laterally extending front waist edge 121 in the front waist region 116 and a longitudinally opposing and laterally extending back waist edge 122 in the back waist region 118. To provide a frame of reference for the present discussion, the diaper 101 and chassis 102 of FIG. 2A are shown with a longitudinal axis 124 and a lateral axis 126. In some embodiments, the longitudinal axis 124 may extend through the front waist edge 121 and through the back waist edge 122. The lateral axis 126 may extend through a first longitudinal or right side edge 128 and through a midpoint of a second longitudinal or left side edge 130 of the chassis 102.

As shown in FIGS. 1 and 2A, the diaper pant 101, including the chassis 102 and the first and second elastic belts 106, 108 may include an inner, body facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper pant 101 may also include other features, such as leg elastics and/or leg cuffs to enhance the fit around the legs of the wearer.

As shown in FIG. 2A, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 are located longitudinally inward from the laterally extending front waist edge 121 in the front waist region 116 and the laterally extending back waist edge 122 in the back waist region 118. When the diaper pant 101 is worn on the lower torso of a wearer, the front waist edge 121 and the back waist edge 122 of the diaper pant 101 may encircle a portion of the waist of the wearer. At the same time, the chassis side edges 128 and 130 may encircle at least a portion of the legs of the wearer. And the crotch region 120 may be generally positioned between the legs of the wearer with the absorbent core 142 extending from the front waist region 116 through the crotch region 120 to the back waist region 118.

Referring to FIG. 2A, the diaper pant 101 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions.

Diaper pants may be manufactured with a ring-like elastic belt 104 and provided to consumers in a configuration wherein the front waist region 116 and the back waist region 118 are connected to each other as packaged, prior to being applied to the wearer. As such, diaper pants 101 may have a continuous perimeter waist opening 110 and continuous perimeter leg openings 112 such as shown in FIG. 1. The ring-like elastic belt 104 is defined by a first elastic belt 106 connected with a second elastic belt 108. As shown in FIG. 2A, the first elastic belt 106 defines first and second opposing end regions 106a, 106b and a central region 106c, and the second elastic 108 belt defines first and second opposing end regions 108a, 108b and a central region 108c. The central region 106c of the first elastic belt 106 is connected with the first waist region 116 of the chassis 102, and the central region 108c of the second elastic belt 108 is connected with the second waist region 118 of the chassis 102. With reference to FIGS. 1 and 2A, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

Figure 3A:
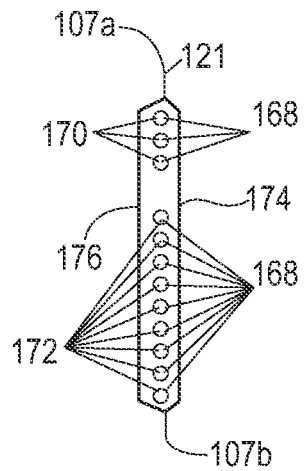
FIG. 3A is a cross-sectional view of the diaper pant of FIGS. 2A and 2B taken along line 3A-3A.
Figure 3B:
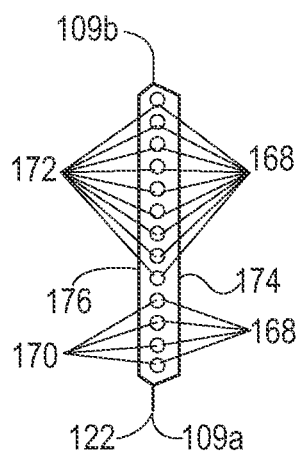
FIG. 3B is a cross-sectional view of the diaper pant of FIGS. 2A and 2B taken along line 3B-3B.

Referring to FIGS. 2A, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 109a may also define the front waist edge 121 and the laterally extending back waist edge 122. The first elastic belt 106 and the second elastic belt 108 may also each include an outer, garment facing layer 174 and an inner, wearer facing layer 176. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer layer 174 and the inner layer 176. The belt elastic material may include one or more elastic elements such as strands, ribbons, or panels extending along the lengths of the elastic belts. As shown in FIGS. 2A, 3A, and 3B, the belt elastic material may include a plurality of elastic strands 168, which may be referred to herein as outer, waist elastics 170 and inner, waist elastics 172. As shown in FIG. 2A, the elastic strands 168 continuously extend laterally between the first and second opposing end regions 106a, 106b of the first elastic belt 106 and between the first and second opposing end regions 108a, 108b of the second elastic belt 108. In some embodiments, some elastic strands 168 may be configured with discontinuities in areas, such as for example, where the first and second elastic belts 106, 108 overlap the absorbent assembly 140. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer 174 and the uncontracted inner layer 176. When the belt elastic material is relaxed, the belt elastic material returns to an unstretched condition and contracts the outer layer 174 and the inner layer 176. The belt elastic material may provide a desired variation of contraction force in the area of the ring-like elastic belt.

It is to be appreciated that the chassis 102 and elastic belts 106, 108 may be configured in different ways other than as depicted in FIG. 2A. For example, FIG. 2B shows a plan view of a diaper pant 101 having the same components as described above with reference to FIG. 2A, except the first laterally extending end edge 144 of the chassis 102 is aligned along and coincides with the outer lateral edge 107a of the first elastic belt 106, and the second laterally extending end edge 146 is aligned along and coincides with the outer lateral edge 109a of the second belt 108.

Components of the disposable absorbent article (i.e., diaper, disposable pant, adult incontinence article, sanitary napkin, pantiliner, etc.) described in this specification can at least partially be comprised of bio-sourced content as described in US 2007/0219521A1 Hird et al published on Sep. 20, 2007, US 2011/0139658A1 Hird et al published on Jun. 16, 2011, US 2011/0139657A1 Hird et al published on Jun. 16, 2011, US 2011/0152812A1 Hird et al published on Jun. 23, 2011, US 2011/0139662A1 Hird et al published on Jun. 16, 2011, and US 2011/0139659A1 Hird et al published on Jun. 16, 2011. These components include, but are not limited to, topsheet nonwovens, backsheet films, backsheet nonwovens, side panel nonwovens, barrier leg cuff nonwovens, super absorbent, nonwoven acquisition layers, core wrap nonwovens, adhesives, fastener hooks, and fastener landing zone nonwovens and film bases.

In at least one embodiment, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B.

In order to apply the methodology of ASTM D6866-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (e.g., Wiley® mill), and a representative sample of suitable mass taken from the randomly mixed particles.

Figure 4A:
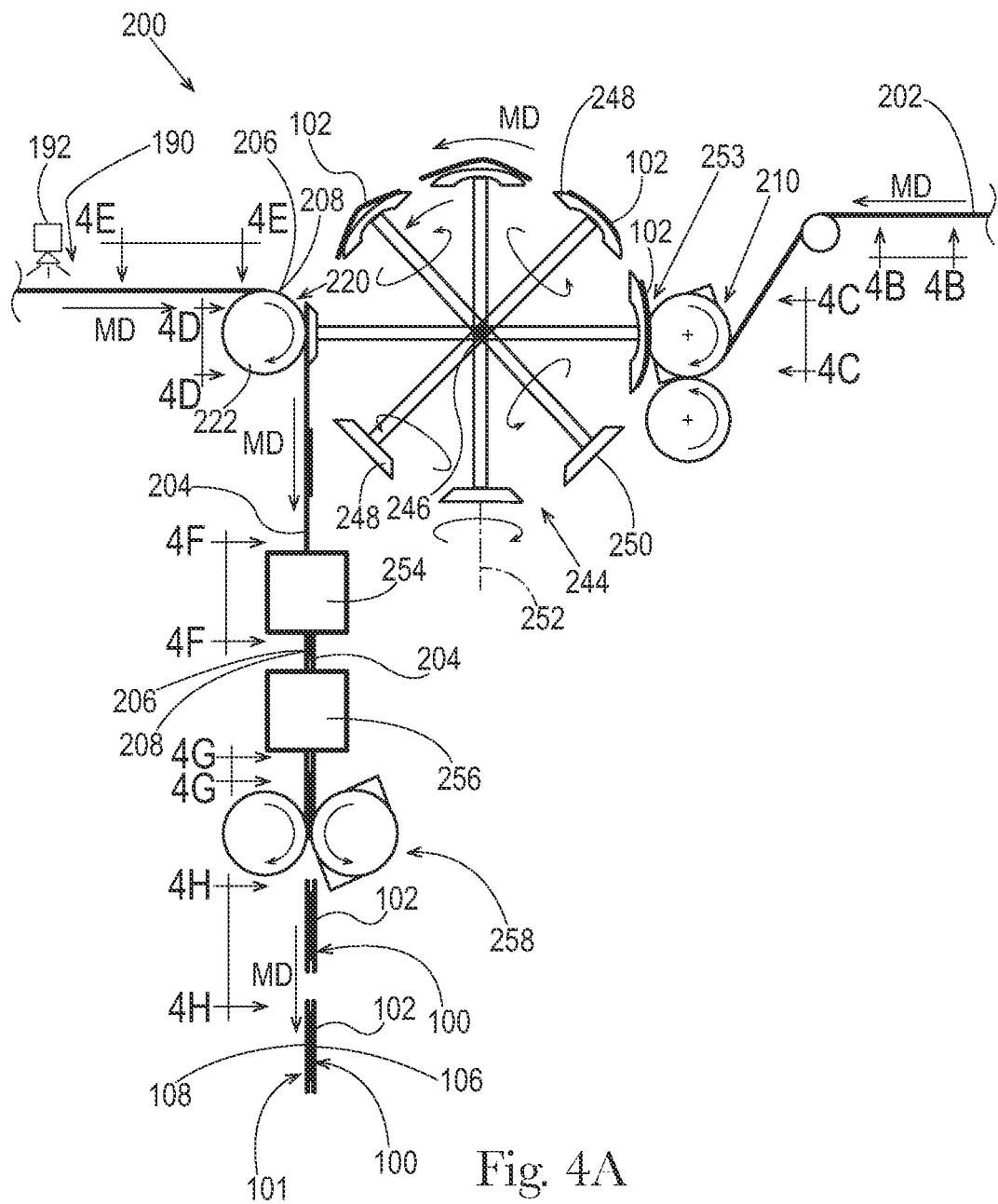
FIG. 4A is a schematic, side elevation view of a converting apparatus.

As previously discussed, the apparatuses and methods of the present disclosure may be used to assemble various components in the manufacture of absorbent articles. For example, FIG. 4A shows a schematic view of a converting apparatus adapted to manufacture diaper pants. The method of operation of the converting apparatus may be described with reference to the various components of the diaper pant 101 described above and shown in FIGS. 1, 2A, and 2B. Although the following methods are provided in the context of the diaper pants shown in FIGS. 1, 2A, and 2B, it is to be appreciated that various types of absorbent articles can be manufactured according the apparatuses and methods disclosed herein, such as for example, the absorbent articles disclosed in U.S. Pat. No. 7,569,039; U.S. Patent Publication No. 2005/0107764; U.S. Patent Application No. 2012/0061016; and U.S. Patent Publication No. 2012/0061015.

With reference to FIG. 4A, and as discussed in more detail below, in operation, a converting apparatus 200 advances a continuous length of chassis assemblies 202 along a machine direction MD such that the longitudinal axis is parallel with the machine direction MD. The continuous length of chassis assemblies 202 are cut into discrete chassis 102. The discrete chassis 102 are then rotated and advanced in the machine direction MD such that the lateral axis is parallel with the machine direction MD. The discrete chassis 102 are combined with continuous lengths of advancing first and second belt substrates 206, 208. The discrete chassis 102 are then folded along the lateral axis to bring the first and second belt substrates 206, 208 into a facing relationship. The first and second belt substrates 206, 208 are then bonded together to form bonded regions. The first and second belt substrates 206, 208 are then cut along the bonded regions to create discrete diaper pants 101.

Figure 4B:
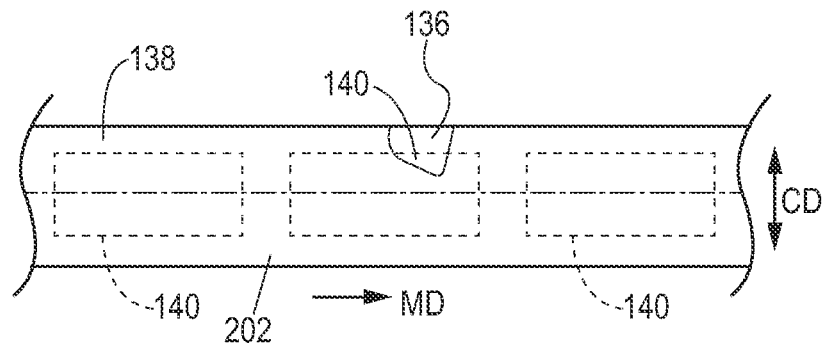
FIG. 4B is a schematic, plan view of a continuous length of chassis assemblies of FIG. 4A taken along lines 4B-4B.

As shown in FIGS. 4A and 4B, a continuous length of chassis assemblies 202 are advanced in a machine direction MD to a cutting device 210 where the continuous length of chassis assemblies 202 is cut into discrete chassis 102. The continuous length of chassis assemblies 202 may include absorbent assemblies 140 sandwiched between topsheet material 138 and backsheet material 136, leg elastics, barrier leg cuffs and the like. A portion of the chassis assembly shown in FIG. 4B is cut-away to show a portion of the backsheet material 136 and an absorbent assembly 140.

After the discrete chassis 102 are cut by the cutting device 210, each chassis 102 are advanced onto a transfer assembly 244. The transfer assembly 244 may include a transfer member 248 having an outer surface 250 on the distal most portion thereof relative to a rotation axis 246. The transfer assembly 244 may rotate about an axis of rotation 246 and the transfer member 248 may rotate about an axis of rotation 252. The outer surface 250 of each transfer member 248 may be flat, or substantially flat, in one or more directions. For example, as shown in FIG. 4A, the outer surface 250 may be flat or substantially flat in one direction, and may be curved in another direction. Substantially flat, as used herein, means the outer surface 250 used to support and transport a discrete article 102 conforms to a plane within about 0-10 mm, and alternatively about 0-5 mm.

Figure 4C:
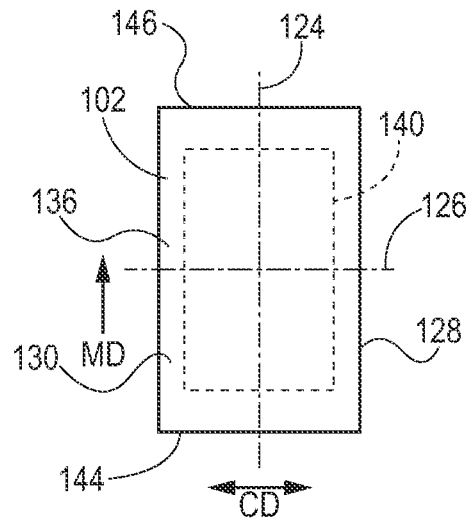
FIG. 4C is a schematic, plan view of a discrete chassis having a longitudinal axis parallel with a machine direction of FIG. 4A taken along line 4C-4C.

The chassis 102 may advance from the cutting device 210 through a nip 253 between the cutting device 210 and the transfer assembly 244 in the orientation shown in FIG. 4C, wherein the longitudinal axis 124 of the chassis 102 is generally parallel with the machine direction MD. The transfer assembly 244 may rotate about the axis of rotation 246 to advance the discrete chassis 102 in the machine direction MD with the second laterally extending end edge 146 as a leading edge and the first laterally extending end edge 144 as the trailing edge. However, it is to be appreciated that in other exemplary configurations, the chassis 102 may be advanced in other orientations. For example, the chassis 102 may be oriented such that the second laterally extending end edge 146 is a trailing edge and the first laterally extending end edge 144 is a leading edge.

Figure 4D:
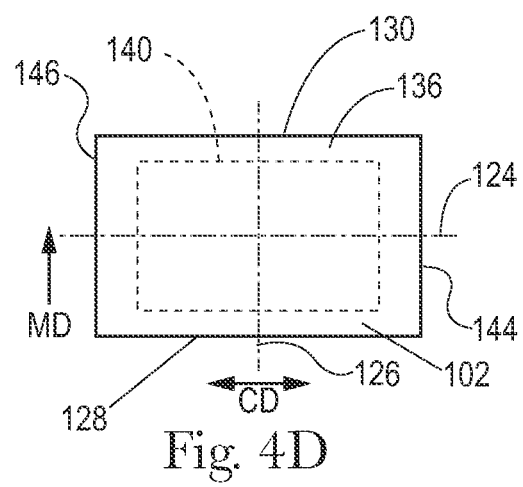
FIG. 4D is a schematic, plan view of a discrete chassis having a lateral axis parallel with the machine direction of FIG. 4A taken along line 4D-4D.

As the transfer assembly 244 advances the discrete chassis 102 in the machine direction MD, the transfer member 248 also rotates the chassis 102 about the axis of rotation 252 to change the orientation of the advancing chassis 102. For example, the transfer member 248 may rotate the chassis from the orientation shown in FIG. 4C to the orientation shown in FIG. 4D, wherein the lateral axis 126 of the chassis 102 generally parallel with the machine direction MD, and wherein the second longitudinal side edge 130 is the leading edge and the first longitudinal side edge 128 is the trailing edge. The transfer assembly 244 may also change the speed at which the chassis 102 advances in the machine direction MD such that the speed of the advancing chassis matches the speed of the advancing first and second belt substrates 206, 208 advancing downstream. It is to be appreciated that various forms of transfer assemblies may be used with the converting apparatus disclosed herein, such as for example, the transfer assemblies disclosed in U.S. Pat. No. 7,587,966; U.S. patent application Ser. No. 13/447,531, filed on Apr. 16, 2012; U.S. patent application Ser. No. 13/447,544, filed on Apr. 16, 2012; U.S. patent application Ser. No. 13/447,568, filed on Apr. 16, 2012; and U.S. patent application Ser. No. 13/447,585, filed on Apr. 16, 2012.

As discussed below with reference to FIGS. 1, 4A, 4D, 4E, and 4F, each chassis 102 is transferred from the transfer assembly 244 and combined with advancing, continuous lengths of first and second elastic belts substrates 206, 208, which are subsequently cut to form first and second elastic belts 106, 108 on absorbent articles 100.

Figure 4E:
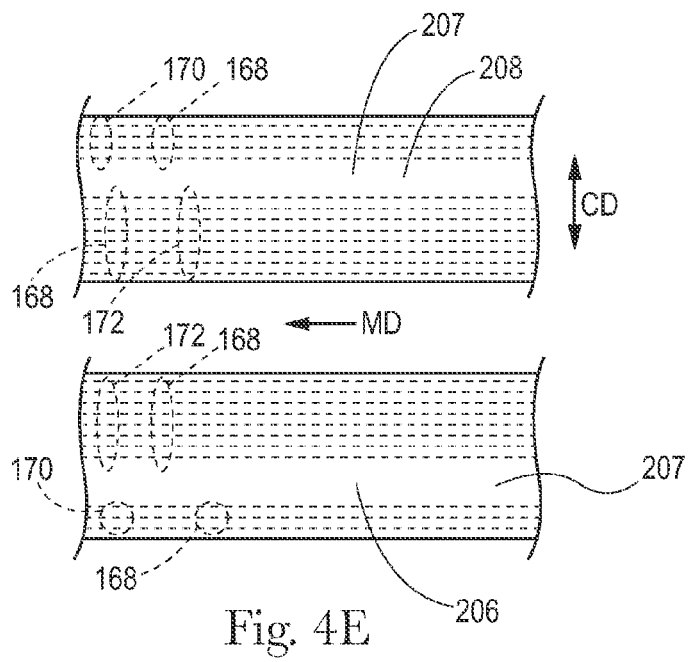
FIG. 4E is a schematic, plan view of continuous lengths of first and second elastic belt substrates of FIG. 4A taken along lines 4E-4E.
Figure 4F:
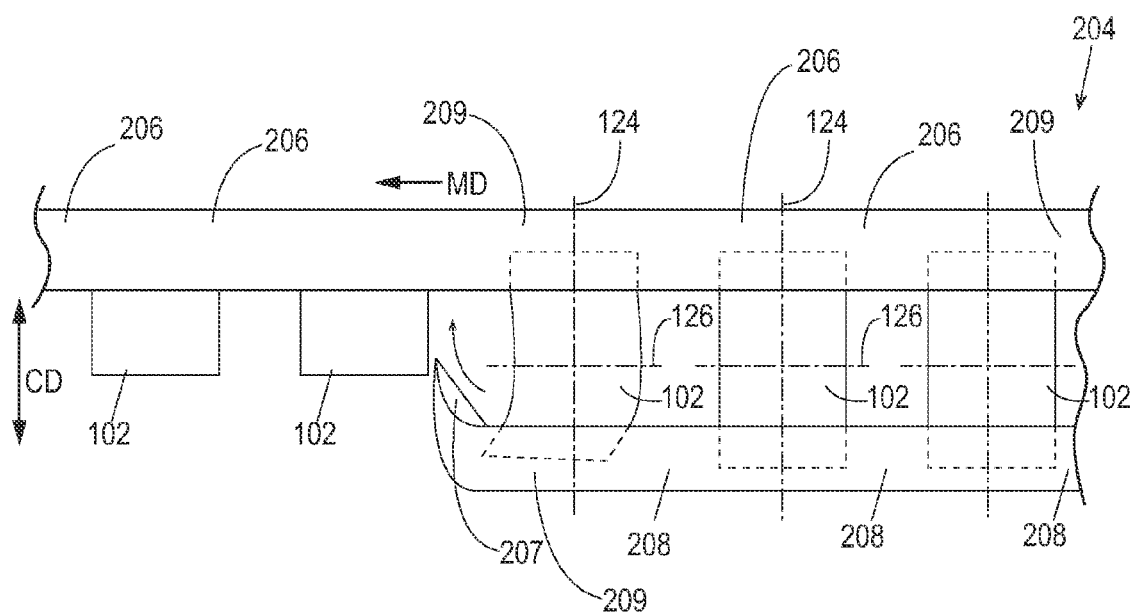
FIG. 4F is a schematic, plan view of a continuous length of diaper pants of FIG. 4A taken along line 4F-4F.

With reference to FIGS. 4A, 4E, and 4F, each chassis 102 is transferred from the transfer assembly 244 to a nip 220 between the transfer assembly 244 and a carrier member 222 where the chassis 102 is combined with first and second belt substrates 206, 208. The first and second belt substrates 206, 208 each define an inner, wearer facing surface 207 and an opposing, outer garment facing surface 209. The inner, wearer facing surface 207 of the first belt substrate 206 may be combined with the outer, garment facing surface 134 of the chassis 102 along the first waist region 116, and the inner, wearer facing surface 207 of the second belt substrate 208 may be combined with the outer, garment facing surface 134 of the chassis 102 along the second waist region 118. As shown in FIG. 4A, adhesive 190 may be intermittently applied by an adhesive applicator 192 to the inner, wearer facing surface 207 of the first and second belt substrates 206, 208 before combining with the discrete chassis 102 at the nip 220 between the transfer assembly 244 and the carrier member 222.

With reference to FIGS. 4A and 4F, a continuous length of absorbent articles 204 are defined by multiple discrete chassis 102 spaced from each other along the machine direction MD and connected with each other by the first and second belt substrates 206, 208. As shown in FIG. 4A, the continuous length of absorbent articles 204 advances from the nip 220 to a folding apparatus 254. At the folding apparatus 254, each chassis 102 is folded in the cross direction CD along a lateral axis 126 to place the first waist region 116, and specifically, the inner, body facing surface 132 into a facing, surface to surface orientation with the inner, body surface 132 of the second waist region 118. The folding of the chassis 102 also positions the inner, wearer facing surface 207 of the second belt substrate 208 extending between each chassis 102 in a facing relationship with the inner, wearer facing surface 207 of the first belt substrate 206 extending between each chassis 102.

Figure 4G:
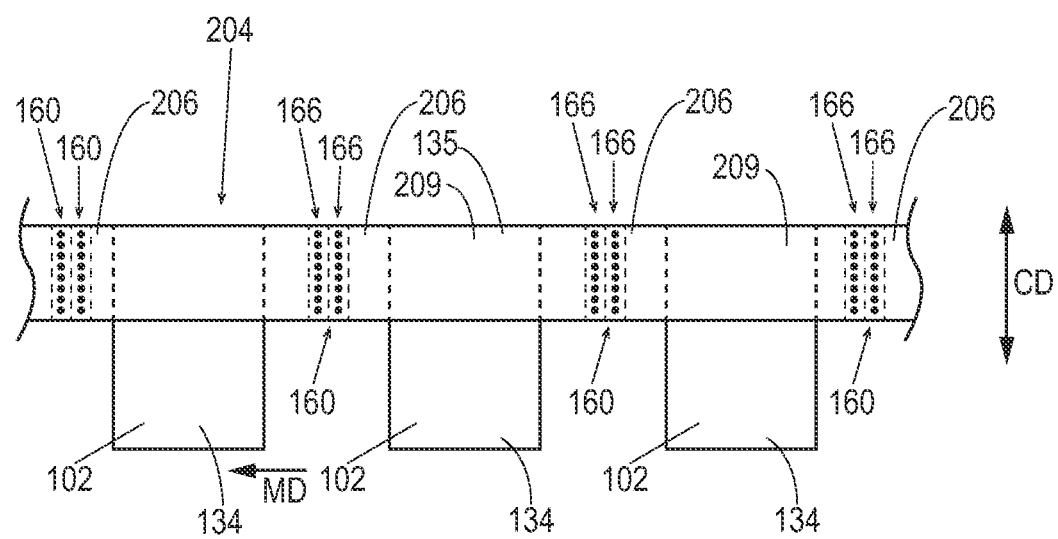
FIG. 4G is a schematic, plan view of a continuous length of folded diaper pants of FIG. 4A taken along line 4G-4G.
Figure 4H:
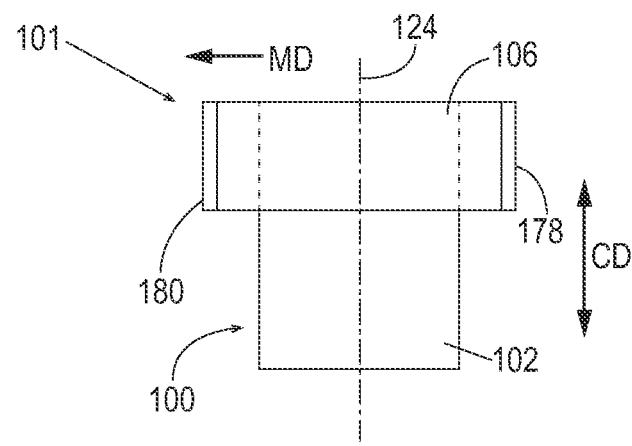
FIG. 4H is a schematic, plan view of a discrete diaper pant of FIG. 4A taken along line 4H-4H.

As shown in FIGS. 4A, 4F, and 4G, the folded discrete chassis 102 connected with the first and second belt substrates 206, 208 are advanced from the folding apparatus 254 to a bonder apparatus 256. The bonder apparatus 256 operates to bond an overlap area 160, thus creating bonded regions 166. The overlap area 160 includes a portion of the second belt substrate 208 extending between each chassis 102 and a portion of the first belt substrate 206 extending between each chassis 102. With reference to FIGS. 4A, 4G, and 4H, the continuous length of absorbent articles 204 are advanced from the bonder apparatus 256 to a cutting device 258 where the bonded regions 166 are cut into along the cross direction CD to create a first side seam 178 on an absorbent article 100 and a second side seam 180 on a subsequently advancing absorbent article.

Figure 5:
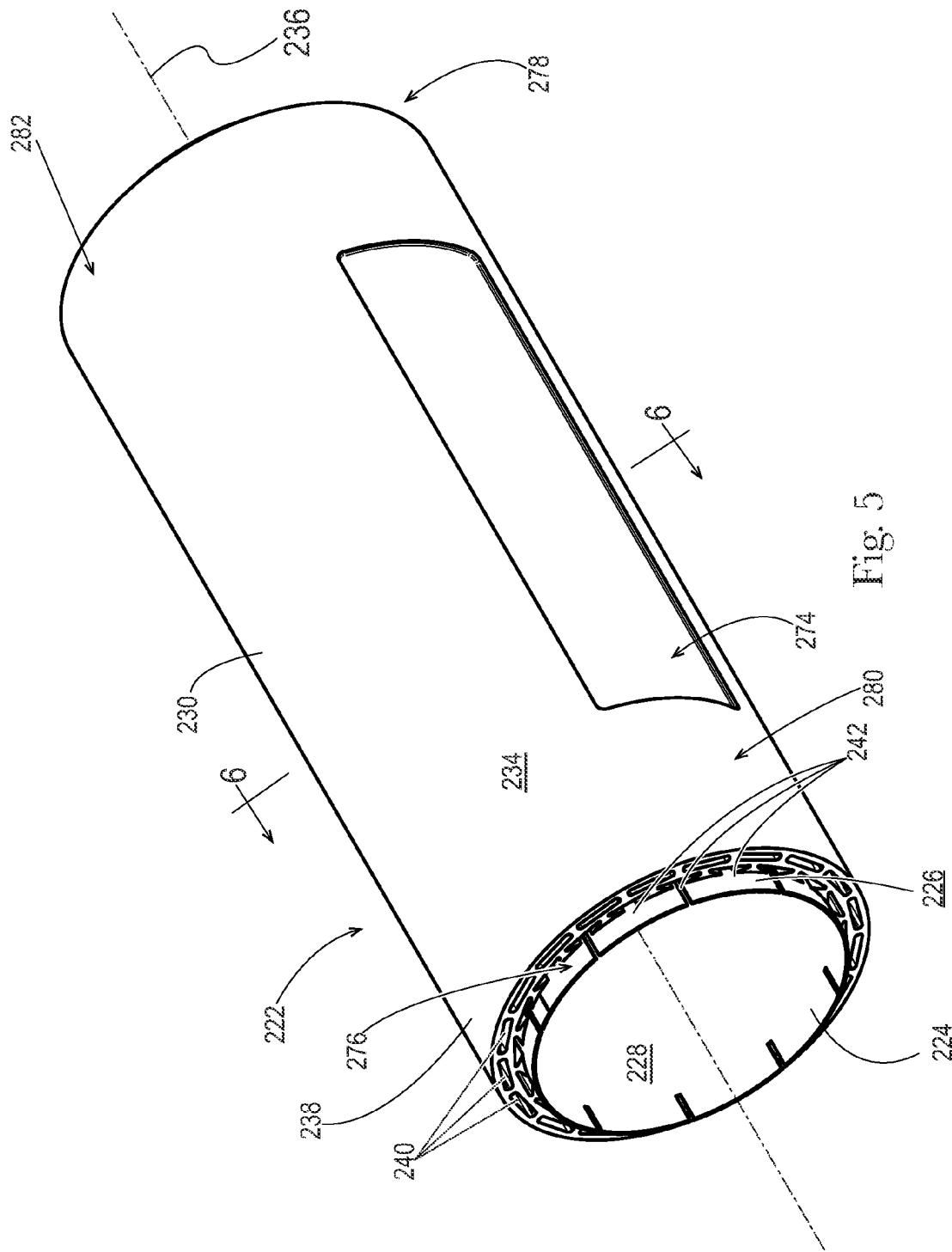
FIG. 5 is a perspective view of a carrier member having a body and a resilient member connected with the body.

As previously mentioned, the present disclosure includes a carrier member 222 for combining the discrete chassis 102 with advancing, first and second belt substrates 206, 208. As shown in FIGS. 5-8, the carrier member 222 may comprise a body 224 having an inner surface 228 and an outer surface 226 and a resilient member 230 connected with the outer surface 226 of the body 224. As shown in FIG. 5, the carrier member 222, including the body 224 and the resilient member 230, may be configured as a cylindrical roll. The resilient member 230 may comprise an inner surface 232, shown in FIGS. 5 and 6 as an inner radial surface, and an outer surface 234, shown in FIGS. 5 and 6 as an outer radial surface. The carrier member 222, including the body 224 and the resilient member 230, may be configured to rotate about an axis of rotation 236.

While it is shown in FIG. 5 that the carrier member 222 may be configured as a cylindrical roll, it is to be appreciated that the carrier member may be configured in various other ways. For example, the carrier member may be configured as a roll, drum, curved conveyor, linear conveyor, or a discrete head configured to follow a curvilinear path.

As shown in FIG. 5, the resilient member 230 may substantially cover the outer surface 226 of the body 224. For example, the resilient member 230 may cover greater than about 70%, greater than about 80%, greater than about 90% or greater than about 95% of the body 224, specifically including 1% increments within the above-specified ranges and any ranges within any of the specified ranges. However, first and second end portions 276, 278 of the body 224 or portions thereof may extend axially beyond the resilient member 230. The resilient member 230 may be connected with the body 224 in various ways. For example, the resilient member 230 may be attached to, adhesively attached to, positioned over, or positioned on the outer surface 226 of the body 224. The resilient member 230 may be configured in the form of a sleeve that fits over the outer surface 226 of the body 224. The resilient member 230 may be configured to rotate with the body 224 of the carrier member 222.

With reference to FIGS. 5-8, the resilient member 230 of the carrier member 222 may comprise a resilient material 238. The resilient material 238 may include various materials that are compressible upon application of an applied force and able to substantially recover to the material's original shape upon removal of the applied force. For example, the resilient material 238 may comprise rubber, silicone rubber, polyurethane, neoprene foam, and the like. The resilient material 238 may impart non-stick characteristics to the outer surface 234 of the resilient member 230. The body 224 of the carrier member 222 may comprise various rigid materials such as stainless steel, tool steel, carbon fiber, fiberglass, and the like.

As shown in FIGS. 5-8, the resilient member 230 may also comprise plurality of voids. In particular, the resilient member 230 may comprise a plurality of intermittently spaced first voids 240 and a plurality of intermittently spaced second voids 242. The plurality of intermittently spaced first voids 240 may be arranged in a first row 260. The first row 260 of first voids 240 may form a curvilinear path that extends circumferentially about the axis of rotation 236 of the carrier member 222. Each first void 240 may be positioned a first radial distance $R_1$ from the axis of rotation 236. The intermittently spaced second voids 242 may be arranged in a second row 262. The second row 262 of second voids 242 may form a curvilinear path that extends circumferentially about the axis of rotation 236. Each second void 242 may be positioned at a second radial distance $R_2$ from the axis of rotation 236. The first radial distance $R_1$ may be greater than the second radial distance $R_2$ such that the first voids 240 are positioned nearer to the outer surface 234 of the resilient member 230 than the second voids 242. Each first and second void 240, 242 may be filled with a fluid, such as air. In some exemplary configurations, the each first and second void 240, 242 may be filled with a porous polymer foam such as neoprene foam or urethane foam, for example. In some exemplary configurations, the resilient member 230 may comprise more than two rows of voids.

As shown in FIGS. 6-8, the first row 260 of first voids 240 may be staggered from the second row 262 of second voids 242. In particular, each first void 240 may be offset from, or intermediate to, the adjacent second voids 242. As shown in FIG. 8, a portion of the first void 240 may overlap a portion of an adjacent second void 242 at the same circumferential position of resilient member 230. The first voids 240 may be circumferentially offset from the adjacent second void 242. Each row of voids may be staggered from each adjacent row of voids.

Figure 9:
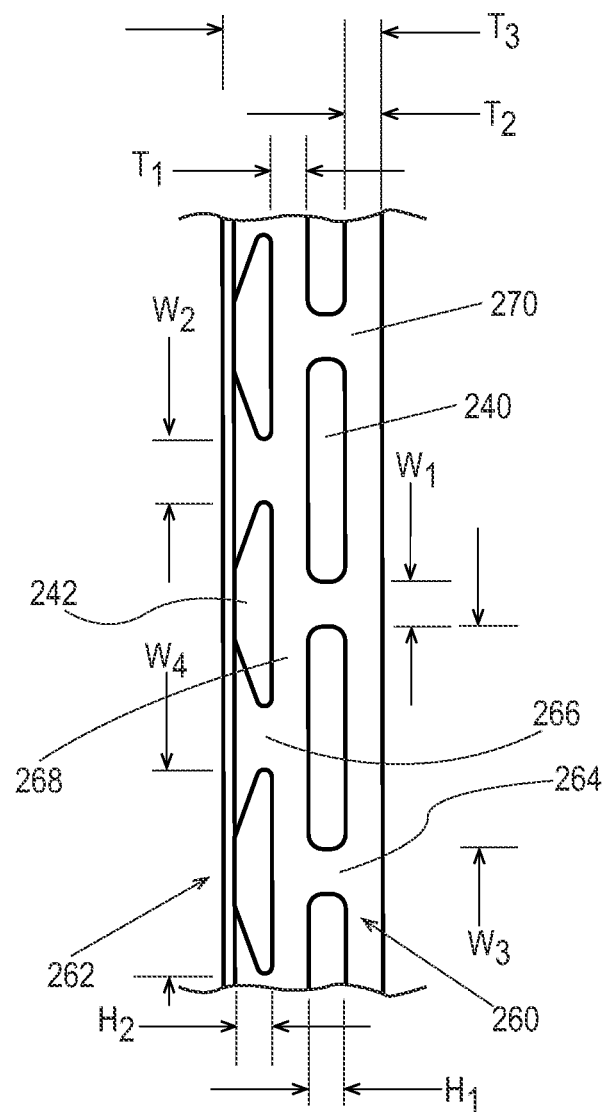
FIG. 9 is a linear, side elevation view of a portion of a carrier member.
Figure 10:
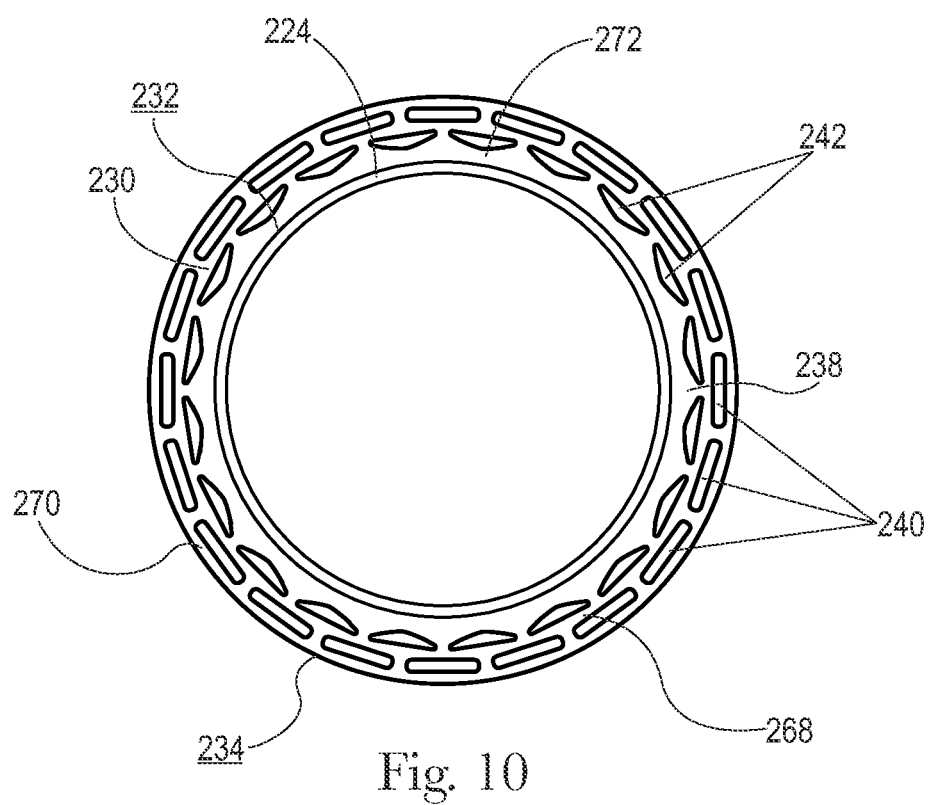
FIG. 10 is a schematic, front elevation view of a carrier member having a body and a resilient member connected with the body.

Each first void 240 may be separated from each adjacent first void 240 by resilient material 238 and each second void 242 may be separated from each adjacent second void 242 by resilient material 238. For example, as shown in FIGS. 6-8, the resilient material 238 may form a first joint 264 between adjacent first voids 240. Similarly, the resilient material 238 may form a second joint 266 between adjacent second voids 242. The first and second joints 264, 266 may have various widths. As shown in FIG. 9, the first joints 264 may have a width $W_1$ of about 1 millimeter (mm) to about 10 mm. The second joints 266 may have a width $W_2$ of about 1 mm to about 10 mm. The first and second joints 264, 266 may have the same, substantially the same, or different widths. The resilient material 238 may form a first wall 268 between the first row 260 of first voids 240 and the second row 262 of second voids 242. The first wall 268 of resilient material 238 may have a thickness $T_1$ of about 2 mm to about 10 mm. A second wall 270 of resilient material 238 may form the outer surface 234 of the resilient member 230. The second wall 270 may have a thickness $T_2$ of about 2 mm to about 10 mm. The thickness $T_1$ of the first wall 268 may be the same, substantially the same, or different than the thickness $T_2$ of the second wall 270. In the exemplary configuration shown in FIGS. 5 and 6, the plurality of second voids 242 combines to form a portion of the inner surface 232 of the resilient member 230. As shown in FIG. 10, in other exemplary configurations, the second voids 242 may be separated from the inner surface 232 by a third wall 272 of resilient material 238.

While it is shown in FIGS. 5 and 7A that the first and second voids 240, 242 are open at first and second end portions 280, 282 of the resilient member 230, it is to be appreciated that in other exemplary configurations, the first and second voids 240, 242 may be closed at the first and second end portions 280, 282 of the resilient member 230 such as shown in FIG. 7B. In such an exemplary configuration, the first and/or second voids 240, 242 may be pressurized by filling the first and/or second voids 240, 242 with a fluid, such as compressed air. Without wishing to be bound by theory, it is believed that pressurizing the first and/or second voids 240, 242 may increase the stiffness of the resilient member 230 and allow for thinner walls and/or joints of the resilient material than a resilient member that has first and/or second voids that are open at the first and second end portions.

With reference to FIGS. 4A, 5, and 6, the carrier member 222 may be positioned adjacent to the transfer assembly 244. The positioning of the carrier member 222 relative to the transfer assembly 244 may result in an installed interference between the transfer members 248 and the carrier member 222 at the nip 220. In operation, as the discrete chassis 102 and the first and second belt substrates 206, 208 advance through the nip 220, the resilient member 230 may be compressed, which, in turn, may provide sufficient compression to join the discrete chassis 102 with the first and second belt substrates 206, 208. In addition, compressing the resilient member 230 may reduce the force that would otherwise be applied to the transfer member 248 at the nip 220 in a configuration wherein the carrier member 222 did not comprise the resilient member 230.

With continuing reference to FIGS. 4A, 5, and 6, as the transfer member 248 compresses the discrete chassis 102 and the first and second belt substrates 206, 208 into the carrier member 222, the resilient material 238 is directed radially inward toward the axis of rotation 236, causing the first and second voids 240, 242 to collapse. By staggering the first and second rows 260, 262 of first and second voids 240, 242, as the transfer member 248 compresses the resilient member 230 near a first joint 264, the resilient material 238 is pushed toward adjacent first voids 240 in the first row 260 and into the adjacent second void 242 in the second row 262. Similarly, as the transfer member 248 compresses the resilient member 230 near a first void 240, the resilient material is compressed into the first void 240 and into portions of the second voids 242 that overlap at the same circumferential portion of the resilient member 230. As a result of staggering the first and second voids 240, 242, the resilient member 230 may experience a relatively uniform compression as the transfer member 248 compresses any portion of the resilient member 230, which, in turn, may result in a relatively uniform bond between the chassis 102 and the first and second belt substrates 206, 208. Furthermore, the force applied to the transfer member 248 may be substantially uniform as the transfer member 248 advances the discrete chassis 102 through the nip 220.

The resilient member may be especially useful in exemplary configurations wherein the outer surface 250 of the transfer member 248 is shaped differently than the shape of the outer surface 234 of the resilient member 230. In such an exemplary configuration, the compressibility of the resilient member 230 may minimize any fluctuations in the amount of force experienced by the transfer member 248 as the chassis 102 advances through the nip 220. For example, in an exemplary configuration such as shown in FIG. 4A wherein the carrier member 222 is configured as a cylindrical roll and the outer surface 250 of the transfer member 248 is flat or substantially flat in at least one direction, the resilient member 230 may compress by different degrees as the chassis 102 advances through the nip, thereby resulting in a substantially uniform force being applied to the transfer member 248.

In an exemplary configuration such as shown in FIG. 7B wherein the first and second voids 240, 242 of the resilient member 230 are closed at the first and second end regions 280, 282 of the resilient member 230, the force applied by the transfer member 248 to the resilient member 230 may cause the pressurized fluid in the first and/or second voids 240, 242 to compress further, which may apply a force to the walls and joints of the resilient member 230, causing the resilient member 230 to return to the original, uncompressed configuration.

As shown in FIG. 5, the outer surface 234 of the resilient member 230 may comprise one or more recessed regions 274. The recessed regions 274 may be configured to match the size of a discrete chassis, or an absorbent assembly of a discrete chassis. The recessed regions 274 may have a depth that matches the thickness of the absorbent assembly of the describe chassis. With reference to FIGS. 4A, 5, and 6, in a configuration wherein the chassis 102, or the absorbent assemblies of the chassis 102, are thicker than the first and second belt substrates 206, 208, the recessed regions 274 may reduce the compressive force applied to the chassis 102 as the chassis 102 advances through the nip 220.

With reference to FIGS. 6-9, the voids may have various dimensions. The first and second voids 240, 242 may have the same dimensions, substantially the same dimensions, or may have different dimensions. For example, the first voids 240 may have a height $H_1$ of about 2 mm to about 10 mm and a width $W_3$ of about 2 mm to about 50 mm. The second voids 242 may have a height $H_2$ of about 2 mm to about 10 mm and a width $W_4$ of about 2 mm to about 50 mm. The resilient member 230 may have a thickness $T_3$ of about 5 mm to about 50 mm. With reference to FIG. 5, each first and second void 240, 242 may extend from the first end portion 276 of the body 224 to the second end portion 278 of the body 224.

With continuing reference to FIGS. 6-9, the voids may be configured to form various cross-sectional shapes. For example, the first and second voids 240, 242 may be rectangular, substantially rectangular, round, substantially round, oval, circular, triangular, substantially triangular, diamond-shaped. The first and second voids 240, 242 may have various other cross-sectional shapes. The first and second voids may have different cross-sectional shapes or may have the same cross-sectional shape. For example, as shown in FIG. 6, the first voids 240 may be substantially rectangular and the second voids 242 may be substantially triangular. However, it is to be appreciated that various other cross-sectional shape combinations are contemplated.

With reference to FIGS. 5 and 6, the first and second voids 240, 242 of the resilient member 230 may result in an overall void area of the resilient member 230 in the range of about 5% void area to about 80% void area, specifically including 1% increments within the specified ranges, and any ranges within the specified ranges.

With continuing reference to FIGS. 5 and 6, if the carrier member 222 is intended to replace an original, different carrier member in a converting apparatus, it may be necessary for the carrier member 222 of the present disclosure to be sized to match the size of the original carrier member. As a result, the design of the resilient member 222, including the thickness of the resilient member 230, and the dimensions, spacing, arrangement, and shape of the first and second voids 240, 242, may be influenced by the size of the original carrier member. For example, the thickness $T_3$ of the resilient member 230 may be fixed. As a result, the thickness $T_3$ of the resilient member 230 may only allow for two rows of voids as a third row of voids may cause the walls between rows of voids to be too thin to withstand the forces that will be applied by the transfer member.

With continuing reference to FIGS. 5 and 6, the resilient material 238 may have a Shore A hardness measured in the range of about 30 to about 75, according to ASTM D2240, specifically reciting all 0.5 increments within the above-specified ranges and any ranges within any of the specified ranges. Various other Shore A hardness values are contemplated.

In various exemplary configurations, the compression force applied to the chassis 102 and the first and second belt substrates 206, 208 at the nip 220 between the carrier member 222 and the transfer assembly 244 may be controlled by the Shore A hardness of the resilient material, the dimensions of the joints and walls of resilient material, the geometry and dimensions of the voids, and/or the percent of void area in the resilient member. Particular geometries of portions of, or all of, the resilient members may allow the resilient members to be compressed easily or to resist compression forces. Geometries and dimensions of the first and second voids may be varied to increase or decrease compression force resistance of the resilient members. Likewise, the hardness and dimensions of the joints and walls of the resilient materials used for the resilient members may allow the resilient members to increase or decrease compression force resistance. Additionally, the number of voids and rows of voids, as well as the dimensions of each void, may be adjusted to control the percent open area of the resilient material to allow the resilient material to increase or decrease compression force resistance.

With reference to FIGS. 5 and 6, the stiffness of the resilient member 230 may be altered by changing the void area, geometry of the first and second voids, the hardness of the resilient material, the dimensions of the joints and walls, the pressure inside of the first and/or second voids, and the like. It is to be appreciated that the stiffness of the resilient member affects the degree of compression of the resilient member 230, and, therefore, the amount of force applied to the transfer member 248. That is, a higher stiffness may result in less compression of the resilient member 230. And, alternatively, a lower stiffness may result in greater compression of the resilient member 230.

The Shore A hardness of the resilient material, the dimensions of the joints and walls of resilient material, the geometry and dimensions of the voids, and/or the percent void area in the resilient material may also affect the amount of deformation the resilient member 230 experiences from the centrifugal force applied to the resilient member 230 as the carrier member 222 rotates about the axis of rotation 236.

With reference to FIG. 4A, in order to control the force applied to the transfer member 248 and the continuous absorbent articles 204, the carrier member 222 may be spring loaded to the transfer assembly 244. In some exemplary configurations, the transfer assembly 244 may be spring loaded to the carrier member 222.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A carrier member configured to receive a discrete article from a transfer assembly, the carrier member comprising a body having an outer surface and a resilient member connected with the outer surface of the body, wherein the resilient member comprises:
    a resilient material;
    a first row of intermittently spaced first voids; and
    a second row of intermittently spaced second voids,
    wherein each first void in the first row is offset from the adjacent second voids in the second row, wherein each first void is separated from each second void by the resilient material, and
    wherein the resilient material has a void area in the range of about 5% void area to about 80% void area.

2. The carrier member of claim 1, wherein the carrier member is a cylindrical roll that is rotatable about an axis of rotation.

3. The carrier member of claim 2, wherein the first row of intermittently spaced first voids extends circumferentially about the axis of rotation, wherein the second row of intermittently spaced second voids extends circumferentially about the axis of rotation.

4. The carrier member of claim 1, wherein the resilient material comprises urethane.

5. The carrier member of claim 1, wherein the resilient material comprises silicone.

6. The carrier member of claim 1, wherein the resilient material forms a first joint between adjacent first voids, wherein the resilient material forms a second joint between adjacent second voids.

7. An apparatus comprising:
    a transfer member having an outer surface; and
    a carrier member comprising a body having an outer surface and a resilient member connected with the outer surface of the body, wherein the carrier member is rotatable about an axis of rotation,
    wherein the resilient member comprises:
        a resilient material;
        a plurality of intermittently spaced first voids extending circumferentially about the axis of rotation at a first radial distance from the axis of rotation; and
        a plurality of intermittently spaced second voids extending circumferentially about the axis of rotation at a second radial distance from the axis of rotation, wherein the first radial distance is greater than the second radial distance,
        wherein the resilient member has a void area in the range of about 5% void area to about 80% void area, and
        wherein a nip is formed between the cylindrical roll and the transfer member.

8. The apparatus of claim 7, wherein the outer surface of the transfer member is substantially flat in at least one direction.

9. The apparatus of claim 7, wherein the resilient material has a Shore A hardness in the range of about 30 to about 75.

10. The apparatus of claim 7, wherein adjacent first voids are separated by the resilient material and adjacent second voids are separated by the resilient material.

11. The apparatus of claim 7, wherein each first void is circumferentially offset from each adjacent second void.

12. The apparatus of claim 7, wherein the resilient material forms a wall that separates the first voids from the second voids.

13. A carrier member configured to receive a discrete article from a transfer assembly, the carrier member comprising a body having an outer surface and a resilient member connected with the outer surface of the body, wherein the carrier member is rotatable about an axis of rotation,
    wherein the resilient member comprises:
        a plurality of intermittently spaced first voids extending circumferentially about the axis of rotation at a first radial distance from the axis of rotation; and
        a plurality of intermittently spaced second voids extending circumferentially about the axis of rotation at a second radial distance from the axis of rotation, wherein the first radial distance is greater than the second radial distance, wherein the first voids are separated from the second voids,
        wherein the resilient member has a void area in the range of about 5% void area to about 80% void area.

14. The carrier member of claim 13, wherein the resilient material has a Shore A hardness in the range of about 30 to about 75.

15. The carrier member of claim 13, wherein the resilient member comprises urethane.

16. The carrier member of claim 13, wherein the resilient member comprises silicone.

17. The carrier member of claim 13, wherein the resilient member further comprises a first joint separating adjacent first voids and a second joint separating adjacent second voids.

* * * * *